(12) United States Patent
Veech (10) Patent No.: US 7,351,736 B2
(45) Date of Patent: Apr. 1, 2008

(54) THERAPEUTIC COMPOSITIONS (II)

(75) Inventor: Richard Lewis Veech, Rockville, MD (US)

(73) Assignee: BTG International Limited, London (GB)

( * ) Notice: Subject to any disclaimer, the term of this patent is extended or adjusted under 35 U.S.C. 154(b) by 319 days.

(21) Appl. No.: 10/734,586

(22) Filed: Dec. 15, 2003

(65) Prior Publication Data

US 2004/0171671 A1    Sep. 2, 2004

Related U.S. Application Data

(63) Continuation of application No. 10/394,644, filed on Mar. 24, 2003, now abandoned, which is a continuation of application No. 09/799,124, filed on Mar. 6, 2001, now abandoned, which is a continuation of application No. PCT/US99/21015, filed on Sep. 15, 1999.

(60) Provisional application No. 60/100,371, filed on Sep. 15, 1998.

(51) Int. Cl.
*A61K 31/357*    (2006.01)

(52) U.S. Cl. .................................... 514/450

(58) Field of Classification Search ................ 514/450
See application file for complete search history.

(56) References Cited

U.S. PATENT DOCUMENTS

| | | | |
|---|---|---|---|
| 5,286,842 A | 2/1994 | Kimura | 528/353 |
| 6,136,862 A * | 10/2000 | Hiraide et al. | 514/578 |
| 6,207,217 B1 | 3/2001 | Peoples et al. | 426/635 |
| 6,323,237 B1 * | 11/2001 | Veech | 514/450 |
| 6,380,244 B2 * | 4/2002 | Martin et al. | 514/449 |
| 2004/0266872 A1* | 12/2004 | Veech | 514/557 |

FOREIGN PATENT DOCUMENTS

| | | |
|---|---|---|
| EP | 0780123 A1 | 6/1997 |
| WO | 00/04895 | 2/2000 |

OTHER PUBLICATIONS

"Heart Failure Ketosis", Lommi et al., Journal of Internal Medicine, 1997, vol. 242, pp. 231-238.*
"Ketosis and Cardiac Failure: Common Signs of a Single Condition", Diltoer et al., European Journal of Emergency Medicine, abstract, 11(3):172-175, 2004.*

* cited by examiner

*Primary Examiner*—Brian Kwon
(74) *Attorney, Agent, or Firm*—Nixon & Vanderhye (57) ABSTRACT

Method of producing a physiologically acceptable ketosis such as to treat a patient in need of therapy for one or more of Amylotrophic lateral sclerosis, Free Radical disease, Heart failure and Duchenne's muscular dystrophy by oral administration to the patient of a cyclic oligomer of formula (I)

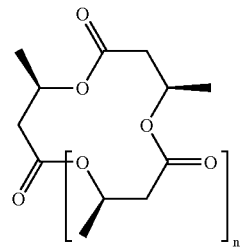

where n is an integer of 1 or more or a complex thereof with one or more cations or a salt thereof, wherein the physiologically acceptable ketosis is characterized by blood levels of (R)-3-hydroxybutyrate of from 0.5 to 20 mM.

3 Claims, 1 Drawing Sheet

FIGURE 1

THERAPEUTIC COMPOSITIONS (II)

This application is a continuation of application Ser. No. 10/394,644, filed Mar. 24, 2003, now abandoned which is a continuation of application Ser. No. 09/799,124, filed Mar. 6, 2001, now abandoned which is a continuation of PCT application No. PCT/US99/21015, filed Sep. 15, 1999, which claims the benefit of U.S. Provisional Application Ser. No. 60/100,371 filed Sep. 15, 1998, the contents of which are hereby incorporated by reference in this application.

The present invention relates to compositions suitable for administration to humans and animals which have the properties of increasing levels of (R)-3-hydroxybutyrate ((R)-3-hydroxybutyric acid or D-β-hydroxybutyrate) when so administered; particularly when administered orally, topically, subcutaneously or parenterally, but most advantageously orally.

Administration of (R)-3-hydroxybutyric acid has a number of beneficial actions on the human and animal body. These include inter alia, increasing cardiac efficiency, eg. in heart failure, provision of an alternative energy source to glucose, eg. in diabetes and insulin resistant states, and treating disorders caused by damage to neuronal cells, eg. CNS cells, particularly by retarding or preventing brain damage such as found in Alzheimer's and Parkinsonism and similar diseases and conditions.

Sodium hydroxybutyrate has been shown to increase cerebral circulation and regional vasomotor reflexes by up to 40% (Biull. Eksp. Biol. Med Vol 88 11, pp555-557). EP 0780123 A1 further teaches use of acetoacetate, β-hydroxybutyrate, monohydric, dihydric or trihydric alcohol esters of these or linear oligomers of 2 to 10 repeats of β-hydroxybutyrate for suppressing cerebral edema, protecting cerebral function, rectifying cerebral energy metabolism and reducing the extent of cerebral infarction.

Intravenous infusion of sodium salts of (R)-3-hydroxybutyrate has been performed on normal human subjects and patients for a number of conditions, eg. those undergoing treatment for severe sepsis in an intensive care unit and is found to be non-toxic and capable of decreasing glucose free fatty acids and glycerol concentration, but ineffective in decreasing leucine oxidation.

The present inventor has further determined that compounds and compositions that raise blood levels of (R)-3-hydroxybutyric acid and/or acetoacetate also have utility in reducing free radicals in vivo, and thus have a place in treatment of free radical associated diseases.

(R)-3-hydroxybutyrate and acetoacetate, commonly referred to as ketone bodies, provide a normal physiological alternative to the usual energy producing substrates, glucose and fatty acids. During prolonged fasting in man fatty acids are converted by liver to (R)-3-hydroxybutyric acid and acetoacetate which can be utilized by most major tissues of the body except liver. Under these conditions, total blood ketone bodies are elevated to about 7 mM. When these are modestly elevated in the blood, extrahepatic tissues such as brain, heart and skeletal muscle utilize these ketone bodies within the mitochondria to provide reducing power in the form of NADH which is the primary substrate of the electron transport system and generator of the energy required for the synthesis of ATP. In turn, generation of mitochondrial NADH by ketones, lowers the ratio of free mitochondrial $[NADP^+]/[NADH]$ ratio and the cytosolic $[NADP^+]/[NADPH]$ ratio to which the mitochondrial $[NADP^+]/[NADH]$ is linked. While the catabolism of ketones reduces mitochondrial $[NADP^+]/[NADH]$ it oxidizes the ratio of mitochondrial [ubiquinone]/[ubiquinol], $[Q]/[QH_2]$. The semiquinone form of ubiquinol is the major source of the generation by mitochondria of superoxide, $O_2$. By decreasing the amount of the reduced form $QH_2$, and its semiquinone, one can decrease the generation of free radicals by mitochondria while at the same time increasing the scavangers of free radicals linked to the NADP system, such as glutathione.

The inventor has thus determined that free radical damage resulting from excess is reduced Q or inhibition of NADH dehydrogenase, such as occurs in MPP induced toxicity, can be reduced by administration of agents which elevate ketone body levels in vivo.

A number of disease processes involve damage by free radicals among which are the neurological diseases: Parkinson's disease, amyotrophic lateral sclerosis, Alzheimer's disease and cerebral ischemia. In addition excessive free radical damage has been implicated as playing a role in coronary reperfusion, diabetic angiopathy, inflammatory bowel disease and pancreatitis.

The inventor's copending WO 98/41201 discloses the administration of linear esters of (R)-3-hydroxybutyric acid and/or acetoacetate in producing elevated levels of the free compounds in vivo. Oral administration of 4 mM solutions of the oligomer tetra-(R)-3-hydroxybutyrate or its acetoacetyl ester was shown to raise blood levels of ketone bodies such that (R)-3-hydroxybutyrate levels could be measured to have increased by 1 to 2 mM for periods in excess of 2 hours.

The inventor has now determined that unexpected advantages are provided when the (R)-3-hydroxybutyric acid component of such composition is administered as a cyclic oligomer. These advantages may include, inter alia, (a) increased efficiency in raising blood (R)-3-hydroxybutyric acid levels such that levels may be increased by more than 2 mM, including attainment of near fasting levels and beyond, (b) maintenance of elevated levels for periods of several hours, (c) ability to be administered without counterion, such as sodium or methylglucamine, where it is desirable not to increase a patient's salt load or where significant dosing is envisaged and (d) relative ease of manufacture of pure compound from polymeric starting materials available through bioculture.

The present application particularly addresses the problem of neurodegenerative diseases, particularly disease where neurons are subject to neurotoxic effects of pathogenic agents such as protein plaques and oxidative damage and further provides compositions for use in treating these and the aforesaid disorders.

In preferred embodiments the present invention provides elevation of blood ketones necessary to correct the defects described above and can be accomplished by parenteral or enteral administration. Particularly it does not require the administration of potentially toxic pharmacological agents. The present invention's improved efficacy in raising levels, particularly blood levels, of ketone bodies provides therapeutic effects of the classical ketogenic diet, which is not itself found to be toxic in children, with none of the side effects that render that unused adults. Furthermore, the inventor has determined that with the correction of the aforesaid metabolic and toxic defects, cytokine responses and the increase in apoptotic peptides in degenerating cells will decrease due to the increase in neuronal cell energy status and the increased trophic stimulation resulting from increased neurotransmitter, eg. acetyl choline, synthesis.

The treatment that the present inventor provides goes beyond ketone body effects on circulation, as it provides treatment for cells that-are unable to function due to neurodegeneration and/or metabolic defects, particularly in metabolism of glucose, eg caused by neurotoxic agents such as peptides, proteins, free radical damage and effect of genetic abnormality. The treatment involves action of ketone bodies on the cells themselves and not the flow of blood to them.

Thus in a first aspect of the present invention there is provided a cyclic ester of (R)-3-hydroxybutyrate of formula (I)

where n is an integer of 1 or more or a complex thereof with one or more cations or a salt thereof for use in therapy or nutrition.

For oral delivery free cyclic oligomer may be preferred. Where cations are present in a complex preferred cations are sodium, potassium, magnesium and calcium and are balanced by physiologically acceptable counter-anion providing a salt complex.

Examples of typical physiologically acceptable salts will be selected from sodium, potassium, magnesium, L-Lysine and L-arginine or eg. more complex salts such as those of methyl glucamine salts Preferably n is an integer from 1 to 200, more preferably from 1 to 20, most preferably from 1 to 10 and particularly conveniently is 1, ie. (R,R,R)-4,8,12-trimethyl-1,5,9-trioxa-dodeca-2,6,10-trione, 2, 3, 4 or 5.

The cyclic esters of the invention are preferably used in the treatment of disease states mediated by free radicals, toxic agents such as peptides and proteins, genetic defects detrimental to nerve cell metabolism, insulin resistance or other glucose metabolism defects or defect inducing states, ischemia, head trauma and/or for increasing cell efficiency, eg. cardiac cell efficiency eg. in heart failure.

A second aspect of the invention provides methods of treating cells that are subject to malfunction due to action of free radicals, toxic agents such as peptides and proteins, genetic defects detrimental to cell metabolism, insulin resistance or other glucose metabolism defects or defect inducing states, ischemia, head trauma and/or for increasing cell efficiency characterised in that it comprises administration of a cyclic oligomer of formula (I). This may include treatment of such disease states in humans and/or animals.

This aspect includes such use as a neuronal stimulant eg capable of stimulating axonal and/or dendritic growth in nerve cells, eg. in hippocampal or substantia nigral cells, in vivo or in vitro, particularly in conditions where neurodegeneration has serious clinical consequences, through its elevating effect on blood and plasma (R)-3-hydroxybutyrate and acetoacetate levels.

A third aspect of the invention provides a method of enteral or parenteral nutrition, preferably oral route nutrition, comprising administration of a cyclic oligomer of formula (I).

A fourth aspect of the invention provides the use of a cyclic ester formula I for the manufacture of a medicament for the treatment of disease states mediated by free radicals, toxic agents such as peptides and proteins, genetic defects detrimental to cell metabolism, insulin resistance or other glucose metabolism defects or defect inducing states, ischemia, head trauma and/or for increasing cell efficiency.

A fifth aspect of the invention provides composition characterised in that it comprises a cyclic oligomer of formula (I) in physiologically acceptable form eg. with a physiologically acceptable carrier.

Particularly the composition is suitable for parenteral or enteral administration, particularly for oral administration. Where the composition is for parenteral use it is sterile and pyrogen free. For oral use the composition may include a foodstuff base and may be in the form of an emulsion or mere admixture with solid food.

Particularly the cyclic oligomer(s) comprise an effective amount of the total composition, eg. at least 2% or more, eg at least 5%, of the composition by weight, more preferably 20% or more and most preferably 50% to 100%. The composition may be adapted for oral, parenteral or any other conventional form of administration.

In preferred forms of all of the aspects of the invention the compound of formula (I) is administered together with a physiological ratio of acetoacetate or a metabolic precursor of acetoacetate. The term metabolic precursor thereof particularly relates to compounds that incorporate acetoacetyl moieties such as acetoacetyl-1,3-butandiol, preferably acetoacetyl-(R)-1,3-butandiol, acetoacetyl-(R)-3-hydroxybutyrate, and acetoacetylglycerol. Esters of any such compounds with monohydric, dihydric or trihydric or higher, eg. glucosyl, alcohols are also envisaged.

In diabetic patients this use of the cyclic oligomers allows maintenance of low blood sugar levels without fear of hypoglycemic complications. In normal non-diabetic subjects the fasting blood sugar is 80 to 90 mg % (4.4-5 mM) rising to 130 mg % (7.2 mM) after a meal. In diabetics 'tight control' of diabetes has long been recommended as a method for retardation of vascular complications but, in practice, physicians have found it difficult to keep blood sugars tightly controlled below 150 mg % (8.3 mM) after eating because of hypoglycaemic episodes. Hypoglycaemic coma occurs regularly in normal subjects whose blood sugar drops to 2 mM. As discussed earlier, (62, 63) in the presence of 5 mM blood ketones there are no neurological symptoms when blood sugars fall to below 1 mM.

The present inventor has determined that supplementing type II diabetics with cyclic oligomers of the invention will allow better control of blood sugar, thus preventing the vascular changes in eye and kidney which occur now after 20 years of diabetes and which are the major cause of morbidity and mortality in diabetics.

Where the therapy is aimed at seizure related disorders, such as refractory epilepsy as is treated by the ketogenic diet, therapy is improved by use of cyclic oligomers, due to the reduction or elimination of both high lipid and carbohydrate content. Such patients include those with genetic defects in the brain glucose transporter system, in glycolysis or in PDH itself such as in Leigh's syndrome, endotoxic shock or high stress states.

Particular disorders treatable with these medicaments are applicable to all conditions involving PDH blockage, including those conditions occuring after head trauma, or involving reduction or elimination of acetyl CoA supply to the mitochondrion such as insulin coma and hypoglycaemia, defects in the glucose transporter in the brain, or elsewhere (80), or in glycolytic enzyme steps.

Where the medicament or nutraceutical comprises acetoacetate it is preferably not stored for a prolonged period or exposed to temperatures in excess of 40° C. Acetoacetate is unstable on heating and decomposes violently at 100° C. into acetone and $CO_2$. In such circumstances it is preferred that acetoacetate is generated by the composition on contact with the bodies metabolic processes. Preferably the composition comprises an ester precursor of actetoacetate.

A sixth aspect of the invention provides a method of treating a human or animal neuronal cell, eg. brain cells, subject to cell damage related disorder, particularly those which lead to cell death, as referred to for the second to fourth aspects, particularly a neurodegenerative disorder eg. such as those related to neurotoxic conditions such as presence of amyloid protein, eg. a memory or movement associated disorder such as Alzheimer's or Parkinson's diseases, or epileptic seizures, comprising administering to that person at least one of the materials for use in the first to fifth aspects of the invention.

The inventor has further determined that ketone bodies, provided by administration of the cyclic oligomers of (R)-3-hydroxybutyric acid in amounts sufficient to raise total blood ketone body concentration to elevated levels result in more than simple maintenance of cell viability but actually improve cell function and growth beyond that of normal, ie. control levels in a manner unrelated to blood flow or nutrition. In this respect the invention further provides use of the cyclic oligomers as agents capable of producing neuronal stimulation, ie. nerve growth factor like activity, increase of metabolic rate and increase of extent of functional features such as axons and dendrites. This aspect of the present invention offers a mechanism for improvement of neuronal function as well as mere retardation of degradation.

The recent work of Hoshi and collaborators (77, 78) strongly suggests that a part of the amyloid protein whose accumulation is the hallmark of Alzheimer's disease, $A\beta_{1-42}$, acts to stimulate mitochondrial histidine protein kinase which phosphorylates and inactivates the pyruvate dehydrogenase multienzyme complex. The PDH complex is a mitochondrial enzyme responsible for the generation of acetyl CoA and NADH from the pyruvate produced by glycolysis within the cytoplasm. The mitochondrial acetyl CoA formed condenses with oxaloacetate to start the Krebs TCA cycle completely combusting pyruvate to $CO_2$ while providing the mitochondria with the reducing power which becomes the substrate for the electron transport system through which the energy required for mitochondrial ATP synthesis is generated Ketone body utilization in brain is limited by the transport, with lesser utilization occurring in the basal ganglion at blood levels below 1 mM (76). However, at levels of 7.5 mM achieved in normal man by prolonged fasting, the rate of ketone body entry into brain is sufficient to take over the majority of cerebral energy needs and to prevent hypoglycemic symptoms, even in the face of blood sugar levels which would normally cause convulsions or coma (63).

In the copending application WO 98/41201, 'Therapeutic compositions', it is the inventor's hypothesis that in Alzheimer's disease, where there is a block at PDH which prevents the normal energy production from glucose, if one can provide elevated, eg. normal fasting levels of ketones, one can bypass the PDH blockade present in these patients thereby preventing cell death due to energy depletion or lack of cholinergic stimulation and thus slow the progression of the memory loss and dementia. Furthermore, utilising the nerve growth/stimulatory effects of the ketone bodies, particularly (R)-3-hydroxybutyrate or a physiological ratio of this with acetoacetate, cells that are still viable can be caused to improve beyond the state to which they have degenerated and accordingly some improvement of function will be seen in patients.

In fed animals and in man the liver content, which is essentially that of blood, of acetoacetate is very low, eg. 0.09 mM and (R)-3-hydroxybutyrate is 0.123 mM but rises after a 48 hour fast to eg. 0.65 mM acetoacetate and 1.8 mM (R)-3-hydroxybutyrate (84). The ketone bodies rise in starvation because the fall in insulin decreases the re-esterification of fatty acids to triglyceride in adipose tissue causing the release of free fatty acids into the blood stream. The released free fatty acids can then be taken up and used as a source of energy by muscle, heart, kidney and liver in the process of β-oxidation. Liver, however, has the capacity to convert the free fatty acids to a metabolic fuel, ketones, for use by extra-hepatic organs including the brain, as an alternative to glucose during periods of fasting. The hepatic synthesis of ketone bodies occurs from mitochondrial acetyl CoA generated during the β-oxidation of fatty acids by liver.

The ketone bodies enter extra-hepatic tissues on the same carrier, where other monocarboxylates can act as competitive inhibitors. Unphysiological isomers such as D-lactate or (S)-3-hydroxybutyrate can also act as competitive inhibitors to ketone body transport. Since ketone body transport across the blood brain barrier is a limiting factor to ketone body utilization in brain (76) every effort should be made to keep the blood concentration of these unphysiological enantiomers at low levels during ketogenic therapy. When blood ketone body concentrations are elevated to levels found in starvation, heart, muscle, kidney and brain utilize ketone bodies as the preferred energy substrate:

The present inventor has thus determined that the mitochondrial acetyl CoA derived from ketone bodies as produced using the cyclic oligomers taught by the present invention can thus replace the acetyl CoA deficiency which occurs during inhibition of PDH multienzyme complex in tissues dependent upon the metabolism of glucose for their supply of metabolic energy. The mitochondrial citrate supplied can also be transported to cytoplasm by the tri or dicarboxylic acid transporter where it can be converted to cytoplasmic acetyl CoA required for the synthesis of acetyl choline. The reactions of the Krebs cycle are shown in Scheme 1 to help illustrate these concepts further.

Ketone bodies, in contrast to free fatty acids, cannot produce acetyl CoA in liver. Since acetyl CoA is the essential precursor of fatty acid, they cannot result in either increased fatty acid or cholesterol synthesis in liver, which usually accounts for over half of the body's synthesis of these two potentially pathogenic materials. Liver is sensitive to the ratio of acetoacetate/(R)-3-hydroxybutyrate presented to it and will alter its mitochondrial free $[NAD^+]/[NADH]$, because of the near equilibrium established by β-hydroxybutyrate dehydrogenase (EC 1.1.1.30) (31).

Inter alia, the aforementioned also indicates that one can provide a method of increasing the efficiency of mitochondrial energy production in a human or animal not suffering from a chronic or acute metabolic disease comprising administering to the human or animal an amount of a cyclic oligomer of formula (I) sufficient to raise blood levels of (R)-3-hydroxybutyrate to from 0.5 to 20 mM.

SCHEME 1

The easiest way to increase blood ketones is starvation. On prolonged fasting blood ketones reach levels of 7.5 mM (62, 63). However, this option is not available on a long term basis, since death routinely occurs after a 60 day fast.

The ketogenic diet, comprised mainly of lipid, has been used since 1921 for the treatment of epilepsy in children, particularly myoclonic and akinetic seizures (109) and has proven effective in cases refractory to usual pharmacological means (71). Either oral or parenteral administration of free fatty acids or triglycerides can increase blood ketones, provided carbohydrate and insulin are low to prevent re-esterification in adipose tissue. Rats fed diets comprised of 70% corn oil, 20% casein hydrolysate, 5% cellulose, 5% McCollum's salt mixture, develop blood ketones of about 2 mM. Substitution of lard for corn oil raises blood ketones to almost 5 mM (Veech, unpublished).

In general the levels of ketone bodies achieved on such diets are about 2 mM (R)-3-hydroxybutyrate and 1 mM acetoacetate while the levels of free fatty acids are about 1 mM. Other variations of composition have been tried including medium chain length triglycerides. In general, compliance with such restricted diets has been poor because of their unpalatability (56). High lipid, low carbohydrate diets also have been tried as therapeutic agents in cancer patients to reduce glucose availability to tumors (88), as weight reducing diets in patients with and without diabetes (74, 112) and to improve exercise tolerance (83).

The limitation of diets which rely upon lipid to raise blood ketones to neurologically effective levels are many. Firstly, levels of ketone bodies on lipid based diets tend to be below 3 mM, significantly lower than the level of 7.5 mM achieved in overweight humans during prolonged fasting. Secondly, unauthorized ingestion of carbohydrate increases insulin secretion and causes a rapid decrease in the hepatic conversion of free fatty acids to ketones with a consequent drop in blood ketones and the diversion of lipid to esterified to triglycerides by adipose tissue. Many anecdotal reports relate the resumption of seizures in children who "broke their diet with birthday cake". Thirdly their unpalatability and the necessity to avoid carbohydrate to sustain high ketone body levels makes such high lipid diets difficult to use in adults in an out patient setting, particularly in societies where traditionally high intake of refined sugars, bread, pasta, rice and potatoes occurs. In practice, the traditional high ketone diet cannot be enforced in patients, other than children beyond the age where all food is prepared at home under strict supervision. Fourthly, ingestion of such large amounts of lipid in the adult population would lead to significant hypertriglyceridemia and hypercholesterolemia with pathological sequelae of increased vascular disease and sporadic hepatic and pancreatic disease, and therefore could not be prescribed on medical grounds. Ingestion of high lipid, low carbohydrate diets were popular in the 1970s for weight reduction in the face of high caloric intake, provided that carbohydrate intake was low. However, because of the increased awareness of the relationship of elevated blood lipids to atherosclerosis the popularity of this diet dropped abruptly.

Substituting glucose in a liquid diet, where glucose accounts for 47% of the caloric content, with racemic 1,3 butandiol caused the blood ketone concentration to rise about 10 fold to 0.98 mM (R)-3-hydroxybutyrate and 0.33 mM acetoacetate (107). These values are slightly less than obtained normally in a 48 hour fast and far below the levels of 7.5 mM obtained in fasting man. Racemic 1,3 butandiol is converted by liver to acetoacetate and both the unnatural L-β and the natural D-β-hydroxybutyrate (respectively (S) 3-hydroxybutanoate and (R)-3-hydroxybutyrate). Although racemic 1,3 butandiol has been extensively studied as a cheap caloric source in animal food and has even been used experimentally in human diets (81, 101) the production of the unnatural L-isomer is likely in the long run to produce significant toxicity as has been shown for the human use of the unnatural D-lactate (64). One disadvantage of administering the unnatural L isomer is that it competes for transport with the natural (R)-3-hydroxybutyrate. Thus provision of the (R) 1,3 butandiol as a precursor of ketone bodies is one possibility that avoids unnecessary administration or production of the unnatural isomer.

The mono and di-aceotacetyl esters of racemic 1,3 butandiol have been suggested as a source of calories and tested in pigs (67). Oral administration of a bolus of a diet containing 30% of calories as the esters produced a brief peak of blood ketones to 5 mM. However, the use of racemic 1,3 butandiol with its production of the abnormal (S) 3-hydroxybutanoate is not to be recommended for the reasons stated above.

While use of racemic 1,3 butandiol in such formulations is not recommended, the esters of (R) 1,3 butandiol can be used, either alone or as the acetoacetate ester.

Studies in rats have shown that feeding racemic 1,3 butandiol caused liver cytosolic [NAD']/[NADH] to decrease from 1500 to about 1000 (87). By comparison, administration of ethanol reduces hepatic [NAD–]/[NADH] to around 200 (106).

Acetoacetate, when freshly prepared, can be used in infusion solutions where it can be given in physiologically normal ratios with (R)-3-hydroxybutyrate to optimum effect (95). Because of manufacturing requirements which currently require long shelf life and hear sterilized fluids, acetoacetate has frequently been given in the form of an ester. This has been done to increase its shelf life and increase its stability to heat during sterilization. In the blood stream, esterase activity has been estimated to be about 0.1 mmol/min/ml and in liver about 15 mmol/min/g (68). In addition to esters combining 1,3 butandiol and acetoacetate there has also been extensive study of glycerol esters of acetoacetate in parenteral (59) and enteral nutrition (82). Such preparations were reported to decrease gut atrophy, due to the high uptake of acetoacetate by gut cells and to be useful in treatment of burns (85).

For preferred embodiments of the present invention, under optimum conditions, a physiological ratio of ketones should be produced through administration of cyclic oligomers and acetoacetate. If it is not, in the whole animal the liver will adjust the ratio of ketones in accordance with its own mitochondrial free [NAD$^+$]/[NADH]. If an abnormal ratio of ketones is given the liver will adjust the ratio, with coincident changes in liver [NADP$^+$]/[NADH]. In the working heart, perfusion with acetoacetate as sole substrate, rapidly induces heart failure (99) in contrast to rat hearts perfused with a mixture of glucose, acetoacetate and (R)-3-hydroxybutyrate, where cardiac efficiency was increased by a physiological ratio of ketone bodies (95).

The cyclic oligomers for use in the present invention are conveniently synthesized from the microorganism produced polyesters. Natural polyesters of (R)-3-hydroxybutyrate are sold as articles of commerce eg. as polymers of 530,000 MW from Alcaligenes eutrophus (Sigma Chemical Co. St. Louis) or as 250,000 MW polymers for sugar beets (Fluka, Switzerland). The bacteria produce the polymer as a source of stored nutrient. The fermentation of these polymers by bacteria was developed in the 1970s by ICI in the UK and Solvay et Cie in Belgium, as a potentially biodegradable plastic for tampon covers and other uses. The system responsible for the synthesis of the poly (R)-3-hydroxybutyrate has now been cloned and variations in the composition of the polymer produced, based on the substrates given to the bacteria. The genes responsible for the synthesis of polyalkanoates have been cloned and expressed in a number of micro-organisms (93, 102, 113) allowing for production of this material in a variety of organisms under extremely variable conditions.

Preferred forms of cyclic oligomeric (R)-3-hydroxybutyrate are, at least in part, readily digestable and/or metabolised by humans or animals. These preferably are of 2 to 200 repeats, typically 2 to 20 and most conveniently from 3 to 10 repeats long, particularly of 3 repeats, ie. the triolide. It will be realised that mixtures of such oligomers may be employed with advantage that a range of uptake characteristics might be obtained. Similarly mixtures with the monomer or linear oligomers or polymers may be provided in order to modify the blood level profile produced.

Cyclic oligomers for use in the invention may be provided, inter alia, by methods described by Seebach et al. Helvetia Chimica Acta Vol 71 (1988) pages 155-167, and Seebach et al. Helvetia Chimica Acta, Vol 77 (1994) pages 2007 to 2033. For some circumstances such cyclic oligomers of 5 to 7 or more (R)-3-hydroxybutyrate units may be preferred as they may be more easily broken down in vivo. The methods of synthesis of the compounds described therein are incorporated herein by reference.

Once the monomer is in the blood stream, and since liver is incapable of metabolizing ketone bodies but can only alter the ratio of (R)-3-hydroxybutyrate/acetoacetate, the ketone bodies are transported to extrahepatic tissues where they can be utilized. The blood levels of ketones achieved are not subject to variation caused by noncompliant ingestion of carbohydrate, as is the case with the present ketogenic diet. Rather, they would simply be an additive to the normal diet, given in sufficient amounts to produce a sustained blood level, typically of between 0.3 to 20 mM, more preferably 2 to 7.5 mM, over a 24 hour period, depending upon the condition being treated. In the case of resistant childhood epilepsy, blood levels of 2 mM are currently thought to be sufficient. In the case of Alzheimer's disease, attempts could even be made to keep levels at 7.5 mM or more, as achieved in the fasting man studies, in an effort to provide alternative energy and acetyl CoA supplies to brain tissue in Alzheimer's patients where PDH capacity is impaired because of excess amounts of $A\beta_{1-42}$ amyloid peptide (77, 78).

The determination by the inventor that (R)-3-hydroxybutyrate and its mixtures with acetoactetate act as a nerve stimulant, eg. nerve growth stimulant and/or stimulant of axon and dendritic growth, opens up the option of raising ketone body levels to lesser degrees than required nutritionally in order to treat neurodegeneration.

Compositions of the invention are preferably sterile and pyrogen free, particularly endotoxin free. Secondly, they are preferably formulated in such a way that they can be palatable when given as an additive to a normal diet to improve compliance of the patients in taking the supplements. The cyclic oligomers are generally smell free. Formulations of the cyclic oligomers of (R)-3-hydroxybutyrate and its mixtures with acetoacetate may be coated with masking agents or may be targeted at the intestine by enterically coating them or otherwise encapsulating them as is well understood in the pharmaceuticals or nutraceuticals art.

Since ketone bodies contain from about 4 to 6 calories/g, there is preferably a compensatory decrease in the amounts of the other nutrients taken to avoid obesity.

Particular advantages of using the cyclic oligomers taught in the present invention are:

1) they can be eaten with a normal dietary load of carbohydrate without decreasing blood ketone body levels which decrease would impair the effects of the treatment,
2) they will not raise blood VLDL and cholesterol, as with current cream and margarine containing diets, thus eliminating the risk of accelerated vascular disease, fatty liver and pancreatitis,
3) they will have a wider range of use in a greater variety of patients, including but not limited to: type II diabetes to prevent hypoglycemic seizures and coma, in Alzheimer's disease and other neurodegenerative states to prevent death of nerve cells eg. hippocampal cells, and in refractory epilepsy due to either decreases in cerebral glucose transporters, defects in glycolysis, or so called Leigh's syndromes with congenital defects in PDH.

The cyclic oligomers of the invention can be used in oral and parenteral use in emulsions, whereas acetoacetate, in the unesterified state, is less preferred as it is subject to spontaneous decarboxylation to acetone with a half time at room temperature of about 30 days. Where the compositions of the invention do include acetoacetate this may be in the form of a precursor. Acetoacetate may conveniently be provided as (R)-3-hydroxybutyrate esters as provided by the copending 'therapeutic compositions' application.

Treatment may comprise provision of a significant portion of the caloric intake of patients with the cyclic (R)-3-hydroxybutyrate oligomer or oligomers formulated to give retarded release, so as to maintain blood ketones in the elevated range, eg. 0.5 to 20 mM, preferably 2-7.5 mM range, over a 24 hour period. Release of the ketone bodies into the blood may be restricted by application of a variety of techniques such as microencapsulation, adsorption and the like which is currently practised in the oral administration of a number of pharmaceutical agents. Enterically coated forms targeting delivery post stomach may be particularly used where the material does not require, or is not susceptible to, hydrolysis in acid environment. Where some such hydrolysis is desired uncoated forms may be used. Some forms may include enzymes capable of cleaving the esters to release the ketone bodies such as those referred to in Doi. Microbial Polyesters.

Preferred cyclic oligomers, eg. the triolide, may be merely added as such to foodstuffs and/or may be supplemented in a treatment regime by other ketone body generators of different release profile such as the monomeric (R)-3-hydroxybutyrate. The latter can be provided as an aqueous solution, eg. as a salt, eg. sodium, potassium, magnesium or calcium salt For a 1500 calorie diet, the human adult patient could consume 198 g of cyclic esters of the present invention per day. For a 2000 calorie diet of the same proportions, one could consume 264 g of ketones per day. On the ketogenic lipid diet blood ketones are elevated to about 2 mM, which proves to be effective to some degree at least in over 60% of children treated. On the ketone diet, ketone levels should be higher because ketones have been substituted at the caloric equivalent of fat, that is 1.5 g of ketone/g of fat. Accordingly, blood ketones should be approximately 3 mM, an effective level in children, but still below the level achieved in fasting man of 7.5 mM.

The advantage of using compounds which directly raised ketone body levels, including the present cyclic oligomers which raise blood levels of ketone bodies themselves are several. Firstly, provision of ketone bodies themselves does not require the limitation of carbohydrate, thus increasing the palatability of the dietary formulations, particularly in cultures where high carbohydrate diets are common. Secondly, ketone bodies can be metabolised by muscle, heart and brain tissue, but not liver. Hence the fatty liver, which may be an untoward side effect of the ketogenic diet, is avoided. Thirdly, the ability to include carbohydrate in the dietary formulations increases the chance of compliance and opens up practical therapeutic approaches to type II diabetics where insulin is high, making the known ketogenic diet unworkable.

The present inventor has determined that, while any elevation of ketone bodies may be desirable, a preferred amount of cyclic ester to be administered will be sufficient, with any acetoacetyl component, to elevate blood ketone body levels to the 0.5 to 20 mM level, preferably to the 2 mM to 7.5 mM level and above, particularly when attempting to arrest the death of brain cells in diseases such as Alzheimer's and Parkinsonism. While dead cells cannot be restored, arrest of further deterioration and at least some restoration of function is to be anticipated.

The total amount of ketone bodies used in treatment of neurodegeneration such as Alzheimer's and Parkinsonism will preferably elevate blood levels of ketone bodies by from 0.5 mM to 20 mM. The present inventor estimates that 200 to 300 g (0.5 pounds) of ketone bodies equivalent per patient per day might be required to achieve this. Where the treatment is through maintenance of cells against the effects of neurotoxin this may be at a level sufficient to act as a significant caloric source, eg. 2 to 7.5 mM in blood. Where it relies on the nerve stimulatory factor effect of the (R)-3-hydroxybutyrate so produced, the amount administered may be lower, eg. to provide 0.2 to 4 mM increase, but can of course be more for this or other disease.

It will be realised that treatment for neurodegenerative diseases such as Alzheimer's or Parkinsonism will most effectively be given soon after identifying patient's with a predisposition to develop the disease. Thus treatment for Alzheimers' most effectively follows a positive test result for one or more conditions selected from the group (i) mutations in the amyloid precursor protein gene on chromosome 21, (ii) mutations in the presenilin gene on chromosome 14, (iii) presence of isoforms of apolipoprotein E. Other tests shown to be indicative of Alzheimer's will of course be applicable.

Following such a positive test result it will be appropriate to prevent the development of memory loss and/or other neurological dysfunction by elevation of the total sum of the concentrations of the ketone bodies (R)-3-hydroxybutyrate and/or acetoacetate in the patient's blood or plasma to say between 1.5 and 10 mM, more preferably 2 to 8 mM, by one of several means. Preferably the patient is fed a diet of sufficient quantities of compound of formula (I), optionally parenterally but preferably and advantageously enterally.

It will be realised that hypoglycemic brain dysfunction will also be treatable using the treatments and compositions and compounds of the present invention. A further property associated with the present treatment will be general improvement in muscle performance.

The provision of cyclic oligomer based foodstuffs and medicaments of the invention is faciliated by the ready availability of a number of relatively cheap, or potentially cheap, starting materials from which cyclic (R)-3-hydroxybutyric acid may be derived (see Microbial Polyesters Yoshiharu Doi. ISBN 0-89573-746-9 Chapters 1.1, 3.2 and 8). The availability of genes capable of insertion into foodstuff generating organisms provides a means for creating products such as yoghurts and cheese that are enriched in the cyclic oligomer-(R)-3-hydroxybutyric acid or, after breakdown with enzymes capable of cleaving such polymers, with the monomeric substance itself (see Doi. Chapter 8).

Methods of preparing poly (R)-3-hydroxybutyrate are not specifically claimed as these are known in the art For example Shang et al, (1994) Appli. Environ. Microbiol. 60: 1198-1205. This polymer is available commercially from Fluka Chemical Co. P1082, cat#81329, 1993-94, 980. Second St. Ronkonkoma N.Y. 11779-7238, 800 358 5287.

The present invention will now be described further by way of illustration only by reference to the following Figures and experimental examples. Further embodiments falling within the scope of the invention will occur to those skilled in the art in the light of these.

EXAMPLES

Example 1

Figure 1:
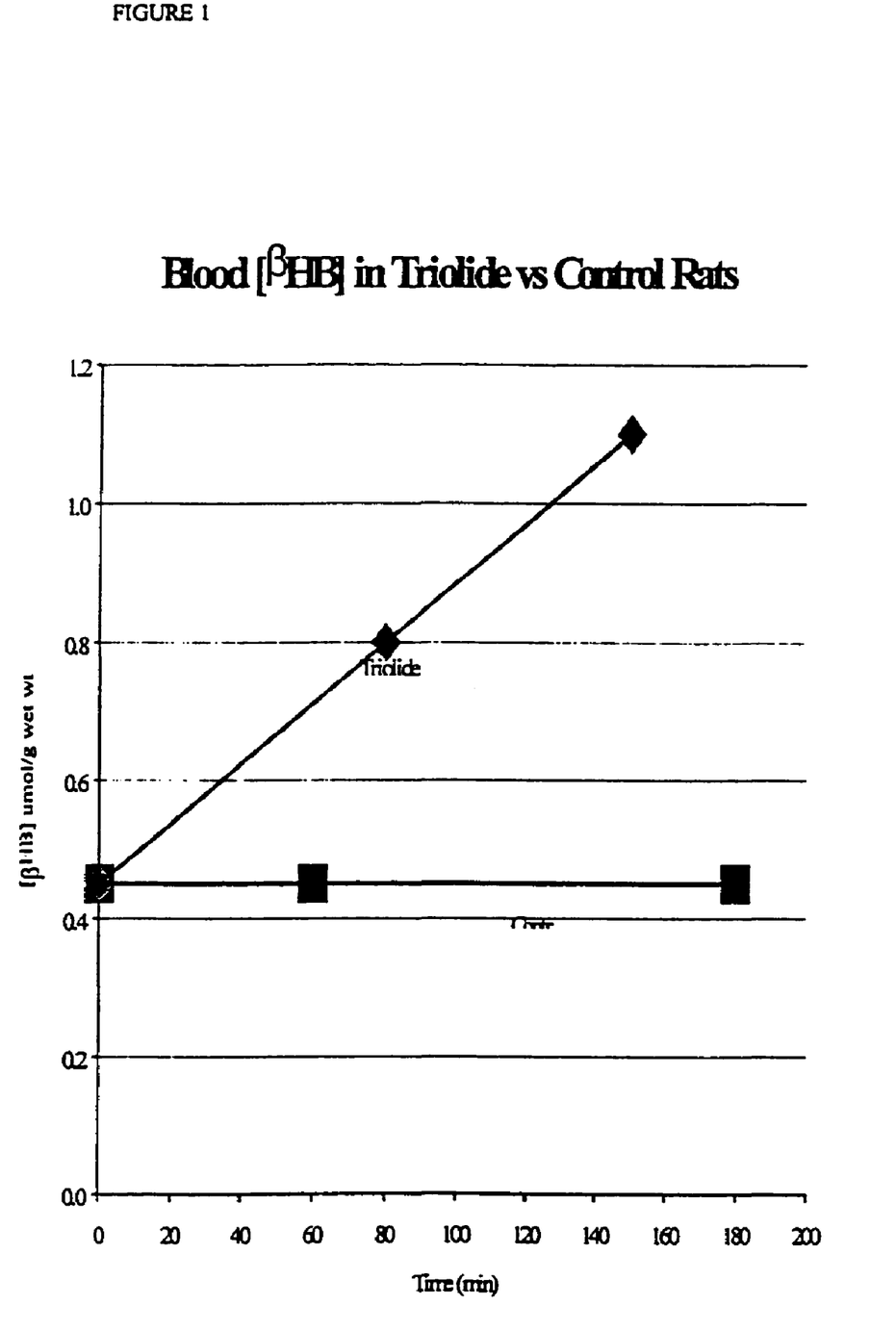
FIG. 1 is a graph showing blood (R)-3-hydroxybutyrate level produced after time after feeding rats with the triolide of (R)-3-hydroxybutyrate, a cyclic oligomer produced in Example 1 in yoghurt and controls fed yoghurt alone.

Preparation of (R,R,R)-4,8,12-trimethyl-1,5,9-trioxadodeca-2,6,10-trione: triolide of (R)-3-hydroxybutyric acid Synthesis was as described in Angew. Chem. Int. Ed. Engl. (1992), 31, 434. A mixture of poly[(R)-3-hydroxybutyric acid] (50 g) and toluene-4-sulphonic acid monohydrate (21.5 g, 0.113 mole) in toluene (840 ml) and 1,2-dichloroethane (210 ml) was stirred and heated to reflux for 20 hours. The water was removed by Dean-stark trap for 15 hours whereafter the brown solution was cooled to room temperature and washed first with a half saturated solution of sodium carbonate then with saturated sodium chloride, dried over magnesium sulphate and evacuated in vacuo. The brown semi-solid residue was distilled using a Kugelrohr apparatus to yield a white solid (18.1 g) at 120-130° C./0.15 mmHg. Above 130° C. a waxy solid began to distill—distillation being stopped at this point. The distilled material had mp 100-102° C. (literature mp 110-110.5° C.). Recrystallisation from hexane gave colourless crystals in yield 15.3 g. Mp=107-108° C.; $[\alpha]_D$-35.1 (c=1.005, CHCl$_3$), (lit.=-33.9). $^1$H NMR (300 MHz, CDCl$_3$): δ=1.30 (d, 9H, CH$_3$); 2.4-2.6 (m, 6H; CH$_2$); 5.31-5.39 (M, 3H; HC—O). $^{13}$C NMR (CDCl$_3$) δ=20.86 (CH$_3$), 42.21 (CH$_2$), 68.92 (CH), 170.12

(CO). Elemental analysis: calculated for $C_{12}H_{18}O_6$: C, 55.81; H, 7.02; Found: C, 55.67; H, 7.15.

Comparative Example 1

Preparation of oligomers of (R)-3-hydroxybutyric acid (R)-3-hydroxybutyrate)

(R)-3-hydroxybutyric acid (Fluka-5.0 g: 0.048 mole), p-toluene sulphonic acid (0.025 g) and benzene (100 ml) were stirred under reflux witha a Dean-Stark trap arrangement for 24 hours. The reaction mixture was cooled and the benzene evaporated in vacuo (0.5 mm Hg). 4.4 g of colourless oil was obtained of which a 20 mg sample was converted to the methyl ester for analysis of number of monomer repeats using NMR. These studies show that the product is a mixture of oligomers of D-β-hydroxybutyrate of average number of repeats 3.75, being mainly a mixture of trimers, tetramers and pentamers with the single most abundant material being the tetramer. The product mixture was soluble in 1 equivalent of sodium hydroxide.

Comparative Example 2

Preparation of acetoacetyl ester of oligomeric (R)-3-hydroxybutyric acid

A further batch of the colourless oil product from Example 1 (4.5 g) was heated for 1 hour at 60° C. with diketene (3.8 g) and sodium actetate (0.045 g) under nitrogen. Further diketene (3.8 g) was added and the reaction heated for a further hour, cooled and diluted with ether, washed with water and then extracted with saturated sodium bicarbonate (5×100 ml). Combined extract was washed with ether then acidified with concentrated HCl (added dropwise). Ethyl acetate extraction (3×50 ml) was followed by drying over magnesium sulphate and evaporation in vacuo. A yellow solid/oil mixture was obtained (7.6 g) which was chromatographed on a silica column using dichloromethane/methanol (98:2) to give a light amber oil product. Faster moving impurities were isolated (1.6 g) and after recolumning carbontetrachloride/methanol (99:1) 0.8 g of oil was recovered which was shown by NMR and Mass spectrometry to be the desired mixture of acetoacetylated oligomers of (R)-3-hydroxybutyrate. The product mixture had an Rf of 0.44 in dichloromethane/methanol (90:1) and was soluble in 1 equivalent of sodium hydroxide.

Both products of Comparative Examples 1 and 2 are amenable to separation of individual components by preparative HPLC.

Example 2

Oral administration of triolide of (R)-3-hydroxybutyrate of Example 1 to rats

The ability of orally administered triolide to raise blood ketone levels was investigated as follows. The day before the experiment commenced, 12 Wistar rats weighing 316+ 10 g were placed in separate cages. They had no access to food for 15 hours prior to presentation with triolide containing compositions, but water was provided ad libitum.

On the morning of the experiment 0.64 g of triolide was mixed with 5 g Co-op brand Black Cherry yoghurt in separate feeding bowls for 9 of the rats. The remaining 3 rats were given 5 g of the yoghurt without the triolide as controls. The yoghurt containing bowls were placed in the cages and the rats timed while they ate. Two of the three control rats ate all the yoghurt and four of the six triolide yoghurt rats ate approximately half the provided amount. The remaining six rats slept.

Control rats (n=2) were killed at 60 and 180 minutes after ingestion of yoghurt while triolide fed rats were killed at 80, 140, 150 and 155 minutes. Blood samples were taken for assay of (R)-3-hydroxybutyrate. Brains were funnel frozen and later extracted in perchloric acid and extracts neutralised and assayed. Blood levels of (R)-3-hydroxybutyrate were measured using a $NAD^-$/EDTA assay of Anal. Biochem (1983) 131, p478-482. 1.0 ml of a solution made up from 2-amino-2-methyl-1-propanol (100 mM pH 9.9, 0.094 g/10 ml), $NAD^+$ (30 mM, 0.199 g/10 ml) and EDTA (4 mM, 0.015 g/10 ml) was added to each of a number of cuvettes and 4 µl sample or (R)-3-hydroxybutyrate control.

The two control rats ate 5.2±0.1 g yoghurt and their plasma (R)-3-hydroxybutyrate concentrations were about 0.45 mM at 60 minutes and 180 minutes. The four triolide fed rats ate 0.39±0.03 g of the triolide and 2.6±0.2 g of yoghurt. Their plasma (R)-3-hydroxybutyrate concentrations were 0.8 mM after 80 minutes and 1.1 mM for the group sacrificed at about 150 minutes. All rats displayed no ill effects from ingestion of triolide. Thus serum (R)-3-hydroxybutyrate was found to be elevated by 0.65 mM by feeding of only 0.4 g triolide. Note, as the rats had been fasted, the initial levels of (R)-3-hydroxybutyrate were elevated from the 0.1 mM fed state to about 0.45 mM.

The test rats thus showed increase in plasma (R)-3-hydroxybutyrate over at least 3 hours with no ill effects. It should be noted that two other rats fed approximately 1.5 g triolide each in 'Hob-Nob' biscuit showed no ill effects after two weeks.

It should be noted that the increased levels of (R)-3-hydroxybutyrate will also be mirrored in acetoacetate levels, not measured here, as there is a rapid establishment of equilibrium between the two in vivo such that acetoacetate levels will be between 40 and 100% of the (R)-3-hydroxybutyrate levels.

Comparative Example 3

Oral administration of (R)-3-hydroxybutyrate, oligomers and acetoacetyl (R)-3-hydroxybutyrate oligomers to rats The ability of orally administered (R)-3-hydroxybutyrate and the linear oligomers of Comparative examples 1 and 2 to raise blood ketone body levels was investigated as follows. Rats were fasted overnight and then gavaged with 100 µl/100 g bodyweight of 4M (R)-3-hydroxybutyrate brought to pH 7.4 using methyl glucamine. Plasma levels of (R)-3-hydroxybutyrate were measured at 0.62 mM after 30 minutes as compared to 3 mM when 9M (R)-3-hydroxybutyrate is used.

This procedure was repeated with 2M solutions of the mixtures (R)-3-hydroxybutyrate oligomers and their acetoacetyl esters described in Comparative Examples 1 and 2. The (R)-3-hydroxybutyrate oligomer (19/1) and the acetoacetyl ester (20/4) were both brought to pH 7.6 with methyl glucamine and the blood (R)-3-hydroxybutyrate level monitored using the aforesaid assay procedure. Increases in serum (R)-3-hydroxybutyrate were shown to be of 0.2 mM to 0.5 mM at 60 and 120 minutes after gavaging.

Example 5

TABLE 2

Sample 1500 calorie ketogenic diet using cyclic oligomer (I) of invention. The cyclic oligomer is assumed to contain 6 kcal/g fats, 9 kcal/g carbohydrate and 4 kcal/g protein. Oligomers have been substituted to give equivalent calories.

|  | Amount (g) | Fat (g) | Protein (g) | CHO (g) | Cyclic (I) (g) |
|---|---|---|---|---|---|
| Breakfast |  |  |  |  |  |
| Egg | 32 | 4 | 4 |  |  |
| apple juice | 70 |  |  | 7 |  |
| ketones | 66 |  |  |  | 66 |
| skim milk | 92 | 0 | 2 | 3 |  |
| Total Breakfast |  | 4 | 6 | 10 | 66 |
| Lunch |  |  |  |  |  |
| lean beef | 12 | 1.75 | 3.5 |  |  |
| cooked carrots | 45 |  | 0.6 | 3 |  |
| canned pears | 40 |  |  | 4 |  |
| ketones | 69.75 |  |  |  | 69.75 |
| skim milk | 92 |  | 2 | 3 |  |
| Total Lunch |  | 1.75 | 6.1 | 10 | 69.75 |
| Supper |  |  |  |  |  |
| Frankfurter | 22.5 | 6 | 3 |  |  |
| cooked broccoli | 50 |  | 1 | 2 |  |
| watermelon | 75 |  |  | 5 |  |
| ketones | 62.25 |  |  |  | 62.25 |
| skim milk | 92 |  | 2 | 3 |  |
| Total Supper |  | 6 | 6 | 10 | 62.25 |
| Daily Total |  | 11.75 | 18.1 | 30 | 198 |

Example 6

Effect of (R)-hydroxybutyrate on hippocampal cells

Methods

Culture Medium and Chemicals

The serum free medium used from 0 to day 4 contained Neurobasal medium with B27 supplement diluted 50 fold (Life Technology, Gaithersburg, Md.) to which was added: 0.5 mM L-glutamine, 25 µM Na L-glutamate, 100 U/ml penicillin and 100 µg/ml streptomycin. After day 4, DMEM/F12 medium containing 5 µM insulin, 30 nM 1-thyroxine, 20 µM progesterone, 30 nM Na selenite 100 U/ml penicillin and 100 µg/ml streptomycin were used.

Hippocampal Microisland Cultures

The primary hippocampal cultures were removed from Wistar embryos on day 18 and dispersed by gentle agitation in a pipette. The suspension was centrifuged at 1,500×g for 10 min and the supernatant discarded. The pellet was resuspended in new media to a final cell count of 0.4-0.5× $10^{-6}$ cells/ml. Ten µl of this suspension was pipetted into the center of poly D-lysine coated culture wells and the plates incubated at 38° C. for 4 hrs and then 400 µl of fresh Neurobasal media was added. After 2 days of incubation, half of the media was exchanged for fresh media and the incubation continued for 2 more days. After day 4, the medium was changed with DMEM/F12 medium containing 5 µM insulin, 30 nM 1-thyroxine, 20 nM progesterone, 30 nM Na selenite 100 U/ml penicillin and 100 µg/ml streptomycin. The wells were divided into 4 groups: half the wells received (R)-3-hydroxybutyrate to a final concentration of 8 mM while and half of the wells received 5 mM amyloid $\beta_{1-42}$ (Sigma). These media were exchanged 2 days later (day 8) and the cells were fixed on day 10 and stained with anti MAP2 (Boehringer Manheim, Indianapolis Ind.) to visualize neurons and vimentin and GFAP (Boehringer) to visualize glial cells.

Results

Cell Counts

Addition of (R)-3-hydroxybutyrate to the incubation resulted in an increase in the neuronal cell number per microisland from a mean of 30 to a mean of 70 cells per microisland. Addition of 5 nM amyloid $\beta_{1-42}$ to the cultures reduced the cell numbers from 70 to 30 cells per microisland, confirming the previous observations of Hoshi et al, that amyloid $\beta_{1-42}$ is toxic to hippocampal neurons. Addition of (R)-3-hydroxybutyrate to cultures containing amyloid $\beta_{1-42}$ increased the cell number from a mean of 30 to 70 cells per microisland. From these data we conclude that addition of substrate level quantities of (R)-3-hydroxybutyrate, to media whose major nutrients are glucose, pyruvate and L-glutamine, slows the rate of cell death in culture. It is further concluded that (R)-3-hydroxybutyrate can decrease the increased rate of hippocampal cell death caused by the addition of amyloid $\beta_{1-42}$ in culture.

The number of dendritic outgrowths and the length of axons were both observed to have increased with presence of (R)-3-hydroxybutyrate, whether $\beta_{1-42}$ was present or not. This is indicative of nerve growth factor like behaviour.

REFERENCES

1. Cheung, J. Y., C. Conover, D. M. Regen, C. F. Whitfield, H. E. Morgan. Effect of insulin on kinetics of sugar transport in heart muscle. Am J Physiol 1978; 234: E70-E78.
2. Simpson, I. A., S. W. Cushman. Hormonal regulation of mammalian glucose transport. Annu Rev Biochem 1986; 55: 1059-1089.
3. Larner, J., J. C. Lawrence, R. J. Walkenbach, P. J. Roach, R. J. Hazen, L. C. Huang. Insulin control of glycogen synthesis. Adv Cyclic Nucleotide Res 1978; 9: 425-439).
4. Denton, R. M., P. J. Randle, B. J. Bridges, R. H. Cooper, A. L. Kerbey, H. T. Pask, D. L. Severson, D. Stansbie, S. Whitehouse. Regulation of mammalian pyruvate dehydrogenase. Mol Cell Biochem 1975; 9: 27-53).
5. Mukherjee, C., R. L. Jungas. Activation of pyruvate dehydrogenase in adipose tissue by insulin. Evidence for an effect of insulin on pyruvate dehydrogenase phosphate phosphatase. Biochem J 1975; 148:229-235.
6. Randle, P. J., R. M. Denton, H. T. Pask, D. L. Severson. Calcium ions and the regulation of pyruvate dehydrogenase. Biochem Soc Symp 1974; 75-88.
7. Sodi-Pallares, D., M. R. Testelli, B. L. Fishleder, A. Bisteni, G. A. Medrano, C. Friedland, A. D. Micheli. Effects of an intravenous infusion of potassium-glucose-insulin solution on the electrographic signs of myocardial infarction. Am J Cardiol 1962; 9: 166-181.
8. Rackley, C. E., R. O. Russell, Jr., W. J. Rogers, J. A. Mantle, H. G. McDaniel, S. E. Papapietro. Clinical experience with glucose-insulin-potassium therapy in acute myocardial infarction. Am Heart J 1981; 102: 1038-1049.
9. Muller, J. E., S. Mochizuki, J. K. Koster, Jr., J. J. Collins, Jr., L. H. Cohn, S. R. Neely. Insulin therapy for depressed myocardial contractility after prolonged ischemia. Am J Cardiol 1978; 41: 1215-1221.
10. Oliver, M. F., L. H. Opie. Effects of glucose and fatty acids on myocardial ischaemia and arrhythmias. Lancet 1994; 343: 155-158.
11. Taegtmeyer, H. The use of hypertonic glucose, insulin, and potassium (GIK) in myocardial preservation. J Appl Cardiol 1991; 6: 255-259.
12. McDaniel, H. G., S. E. Papapietro, W. J. Rogers, J. A. Mantle, L. R. Smith, R. O. Russell, Jr., C. E. Rackley. Glucose-insulin-potassium induced alterations in individual plasma free fatty acids in patients with acute myocardial infarction.
Am Heart J 1981; 102: 10-15.
13. Cross, H. R., K. Clarke, L. H. Opie, G. K. Radda. Is lactate-induced myocardial ischaemic injury mediated by decreased pH or increased intracellular lactate?
J Mol Cell Cardiol 1995; 27: 1369-1381.
14. Cahill, G. F. Jr. Starvation in man. N Engl J Med 1970; 282: 668-675.
15. Sato, K., Y. Kashiwaya, C. A. Keon, N. Tsuchiya, M. T. King, G. K. Radda, B. Chance, K. Clarke, R. L. Veech. Insulin, ketone bodies, and mitochondrial energy transduction. FASEB J 1995; 9: 651-658.
16. Kashiwaya, Y., K. Sato, N. Tsuchiya, S. Thomas, D. A. Fell, R. L. Veech, J. V. Passonneau. Control of glucose utilization in working perfused rat heart.
J Biol Chem 1994; 269: 25502-25514.
17. Clarke, K., Y. Kashiwaya, M. T. King, D. Gates, C. A. Keon, H. R. Cross, G. K. Radda, R. L. Veech. The β/α peak height ratio of ATP: a measure of free [$Mg^{2+}$] using $^{31}P$ NMR. J Biol Chem 1996; 271: 21142-21150.
18. Veloso, D., R. W. Guynn, M. Oskarsson, R. L. Veech. The concentrations of free and bound magnesium in rat tissues. Relative constancy of free $Mg^{2+}$ concentrations. J Biol Chem 1973; 248: 4811-4819.
19. Chance, B., J. S. J. Leigh, J. Kent, K. McCully, S. Nioka, B. J. Clark, J. M. Maris, T. Graham. Multiple controls of oxidative metabolism in living tissues as studied by phosphorus magnetic resonance. Proc Natl Acad Sci USA 1986; 83: 9458-9462.
20. Veech, R. L., J. W. R. Lawson, N. W. Cornell, H. A. Krebs.
Cytosolic phosphorylation potential. J Biol Chem 1979; 254: 6538-6547.
21. Passonneau, J. V., J. P. Schwartz, D. A. Rottenberg. The partial purification and properties of pig brain alycogen synthase. J Biol Chem 1975; 250: 2287-2292.
22. Michaelis, L., M. L. Menten. Die Kinetik der Invertinwirkung.
Biochem Z 1913; 49: 333-369.
23. Haldane, J. B. S., Enzymes. London: Longmans, Green and Co. 1930: 74-92.
24. Kacser, H., J. A. Burns. The control of flux. Symp Soc Ecp Biol 1973; 27: 65-104.
25. Purich, D. L., H. J. Fromm, F. B. Rudolph. The hexokinases: kinetic, physical, and regulatory properties. Adv Enzymol Relat Areas Mol Biol 1973; 39: 249-326.
26. Casazza J. P., R. L. Veech. The interdependence of glycolytic and pentose cycle intermediates in ad libitum fed rats. J Biol Chem 1986; 261: 690-698.
27. Randle, P. J. Metabolic fuel selection: general integration at the whole-body level. Proc Nutr Soc 1995; 54: 317-327.
28. Williamson, J. R., H. A. Krebs. Acetoacetate as fuel of respiration in the perfused rat heart. Biochem J 1961; 80: 540-547.
29. Taegtmeyer, H., R. Hems, H. A. Krebs. Utilization of energy-providing substrates in the isolated working rat heart. Biochem J 1980; 186: 701-711.
30. Halestrap, A. P., R. M. Denton. The specificity and metabolic implications of the inhibition of pyruvate transport in isolated mitochondria and intact tissue preparations by K-Cyano-4-hydroxycinnamate and related compounds. Biochem J 1975; 148: 97-106.
31. Williamson, D. H., P. Lund, H. A. Krebs. The redox state of free nicotinamide-adenine dinucleotide in the cytoplasm and mitochondria of rat liver.
Biochem J 1967; 103: 514-527.
32. Krebs, H. A., R. L. Veech. The energy and metabolic control in mitochondria. Adriatica Editrice: Bari, 1969: 329-382.
33. Ozawa, K., H. Aoyama, K. Yasuda, Y. Shimahara, T. Nakatani, J. Tanaka, M. Yamamoto, Y. Kamiyama, T. Tobe. Metabolic abnormalities associated with postoperative organ failure. A redox theory. Arch Surg 1983; 118: 1245-1251.
34. Tanaka, A., T. Kitai, A. Tokuka. T. Inomoto, H. J. Kim, K. Tanaka, Y. Yamaoka, K. Ozawa. Increased span of oxido-reduction states between pyridine nucleotide and cytochrome c oxidase in the regenerating rabbit liver as measured by arterial ketone body ratio and near-infrared spectroscopy. Res Exp Med (Berl) 1993; 193: 353-359.
35. Veech, R. L., D. N. Gates, C. W. Crutchfield, W. L. Gitomer, Y. Kashiwaya, M. T. King, R. Wondergem. Metabolic hyperpolarization of liver by ethanol: The importance of $Mg^{2+}$ and $H^+$ in determining impermeant intracellular anionic charge and energy of metabolic reactions. Alcohol Clin Exp Res 1994; 18: 1040-1056.
36. Lawson, J. W. R., R. L. Veech. Effects of pH and free $Mg^{2+}$ on the Keq of the creatine kinase reaction and other phosphate hydrolyses and phosphate transfer reactions. J Biol Chem 1979; 254: 6528-6537.
37. Hochachka, P. W., C. M. Clark, J. E. Holden, C. Stanley, K. Ugurbil, R. S. Menon. $^{31}P$ magnetic resonance spectroscopy of the Sherpa heart: a phosphocreatine/adenosine triphosphate signature of metabolic defense against hypobaric hypoxia. Proc Natl Acad Sci USA 1996; 93: 1215-1220.
38. Klingenberg, M. Metabolite transport in mitochondria: an example for intracellular membrane function. Essays Biochem 1970; 6: 119-159.
39. Coty, W. A., P. L. Pedersen. Phosphate transport in rat liver mitochondria, Kinetics and energy requirements. J Biol Chem 1974; 249: 2593-2598.
40. Masuda, T., G. P. Dobson, R. L. Veech. The Gibbs-Donnan near-equilibrium system of heart. J Biol Chem 1990; 265: 20321-20334.
41. Romani, A., A. Scarpa. cAMP control of $Mg^{2+}$ homeostasis in heart and liver cells.
Magnes Res 1992; 5: 131-137.
42. Veech, R. L., Y. Kashiwaya, M. T. King. The resting potential of cells are measures of electrical work not of ionic currents. Int Physiol Behav Sci 1995; 30: 283-306.
43. Denton, R. M., J. G. McCormack, P. J. Midgley, G. A. Rutter. Hormonal regulation of fluxes through pyruvate dehydrogenase and the citric acid cycle in mammalian tissues. Biochem Soc Symp 1987; 54: 127-143.

44. Saladin, R, P. De Vos, M. Guerre-Millo, A. Leturque, J. Girard, B. Staels, J. Auwerx. Transient increase in obese gene expression after food intake or insulin administration. Nature 1995; 377: 527-529.

45. Apstein, C. S., F. N. Gravino, C. C. Haudenschild. Determinants of a protective effect of glucose and insulin on the ischemic myocardium. Effects on contractile function, diastolic compliance, metabolism, and ultrastructure during ischemia and reperfusion. Circ Res 1983; 52: 515-526.

46. Mantle, J. A., W. J. Rogers, L. R. Smith, H. G. McDaniel, S. E. Papapietro, R. O. Russell Jr., C. E. Rackley. Clinical effects of glucose-insulin-potassium on left ventricular function in acute myocardial infarction: results from a randomized clinical trial. Am Heart J 1981; 102: 313-324.

47. Owen, O. E., A. P. Morcran, H. G. Kemp, J. M. Sullivan, M. G. Herrera, G. F. Cahill, Jr. Brain metabolism during fasting. J Clin Invest 1967; 46: 1589-1595.

48. Veech, R. L. The toxic impact of parenteral solutions on the metabolism of cells: a hypothesis for physiological parenteral therapy. Am J Clin Nutr 1986; 44: 519-551;

49. Chan, L., J. Slater, J. Hasbargen, D. N. Herndon, R. L. Veech, S. Wolf. Neurocardiac toxicity of racemic D,L-lactate fluids. Integr Physiol Behav Sci 1994; 29: 383-394.

50. ISIS4. A randomised factorial trial assessing early oral captopril, oral mononitrate, and intravenous magnesium sulphate in 58,050 patients with suspected acute myocardial infarction. Lancet 1995; 345: 669-685.

51. Seelig, M. S., R. J. Elin. Is there a place for magnesium in the treatment of acute myocardial infarction? Am Heart J 1996; 132: 471-477.

52. McLean, R. M. Magnesium and its therapeutic uses: a review. Am J Med 1994; 96: 63-76

53. Ma, J., A. R. Folsom, S. L. Melnick, J. H. Eckfeldt, A. R. Sharrett, A. A. Nabulsi, R. G. Hutchinson, P. A. Metcalf. Associations of scrum and dietary magnesium with cardiovascular disease, hypertension, diabetes, insulin, and carotid arterial wall thickness: the ARIC study. Atherosclerosis Risk in Communities Study. J Clin Epidemiol 1995; 48: 927-940.

54. Ozono, R., T. Oshima, H. Matsuura, Y. Higashi, T. Ishida, M. Watanabe, M. Yoshimura, H. Hiraga, N. Ono, G. Kajiyama. Systemic magnesium deficiency disclosed by magnesium loading test in patients with essential hypertension. Hypertens Res 1995; 18: 39-42.

55. Rasmussen, H. S., P. McNair, L. Goransson, S. Balslov, O. G. Larsen, P. Aurup. Magnesium deficiency in patients with ischemic heart disease with and without acute myocardial infarction uncovered by an intravenous loading test. Arch Intern Med 1988; 148: 329-332.

56. Amari, A., N. C. Grace, W. W. Fisher. Achieving and maintaining compliance with the ketogenic diet. J Appl Behav Anal 28: 341-342, 1995.

57. Bartus, R. T., R. L. Dean, 3d, B. Beer, A. S. Lippa. The cholinergic hypothesis of geriatric memory dysfunction. Science 217: 408-414, 1982.

58. Beylot, M., D. Chassard, C. Chambrier, M. Guiraud, M. Odeon, B. Beaufrere, P. Bouletreau. Metabolic effects of a (R)-3-hydroxybutyrate infusion in septic patients: inhibition of lipolysis and glucose production but not leucine oxidation. Crit Care Med 22: 1091-1098, 1994.

59. Birkhahn, R. H., J. R. Border. Intravenous feeding of the rate with short chain fatty acid esters. II Monoacetoacetin. Am J Clin Nutr 31: 436-441, 1978

60. Brashear, A., G. A. Cook. A spectrophotometric, enzymatic assay for D-3-hydroxybutyrate that is not dependent on hydrazine. Anal Biochem 131: 478-482, 1983.

61. Brion, J. P. The neurobiology of Alzheimer's disease. Acta Clin Belg 51: 80-90 1996.

62. Cahill, G. F., Jr. Starvation in man. N Engl J Med 282: 668-675, 1970.

63. Cahill, G. F., Jr., T. T. Aoki. Alternative Fuel Utilization in Brain. In: Cerebral metabolism and neural function, edited by J. V. Passonneau, R. A. Hawkins, W. D. Lust, and F. A. Welsh, Baltimore, Williams & Wilkins, 1980, p. 234-242.

64. Chan, L., J. Slater, J. Hasbargen, D. N. Herndon, R. L. Veech, S. Wolf. Neurocardiac toxicity of racemic D,L-lactate fluids, Integr Physiol Behav Sci 29: 383-394, 1994.

65. Chartier-Harlin, M. C., F. Crawford, H. Houlden, A. Warren, D. Hughes, L. Fidani, A. Goate, M. Rossor, P. Roques, J. Hardy Early-onset Alzheimer's disease caused by mutations at codon 717 of the beta-amyloid precursor protein gene. Nature 353: 844-846, 1991.

66. Corder, E. H., A. M. Saunders, W. J. Strittmatter, D. E. Schmechel, P. C. Gaskell, G. W. Small, A. D. Roses, J. L. Haines, M. A. Pericak-Vance. Gene dose of apolipoprotein E type 4 allele and the risk of Alzheimer's disease in late onset families (see comments), Science 261: 921-923, 1993.

67. Desrochers, S., P. Dubreuil, J. Brunet, M. Jette, F. David, B. R. Landau, H. Btunengraber. Metabolism of (R,S)-1, 3-butanediol acetoacetate esters, potential parenteral and enteral nutrients in conscious pigs. Am J Physiol 286: E660-7, 1995.

68. Desrochers, S., K. Quinze, H. Dugas, P. Dubreuil, C. Bomont, F. David, K. C. Agarwal, A. Kumar, M. V. Soloviev, L. Powers, B. R. Landau, H. Brunengraber. (R.S.) 1,3 butanediol acetoacetate esters, potential alternatives to lipid emulsions for total parenteral nutrition. J Nutr Biochem 6: 109-116, 1995.

69. Feany, M. B., D. W. Dickson. Neurodegenerative disorders with extensive tau pathology: a comparative study and review. Ann Neurol 40: 139-148, 1996.

70. Fox, N. C., E. K. Warrington, P. A. Freeborough, P. Hartikainen, A. M. Kennedy, J. M. Stevens, M. N. Rossor. Presymptomatic hippocampal atrophy in Alzheimer's disease. A longitudinal MRI study. Brain 119: 2001-2007, 1996

71. Freeman, J. M., E. P. G. Vining. Intractable epilepsy. Epilepsia 33: 1132-1136, 1992.

72. Goate, A., M. C. Chartier-Harlin, M. Mullan, J. Brown, F. Crawford, L. Fidani L. Giuffra, A. Haynes, N. Irving, L. James. Segregation of a missense mutation in the amyloid precursor protein gene with familial Alzheimer's disease (see comments). Nature 349: 704-706, 1991.

73. Graham, D. I., S. M. Gentleman, J. A. Nicoll, M. C. Royston, J. E. McKenzie, G. W. Roberts, W. S. Griffin. Altered beta-APP metabolism after head injury and its relationship to the aetiology of Alzheimer's disease. Acta Neurochir Suppl (Wien). 66: 96-102, 1996.

74. Gumbiner, B., J. A. Wendel, M. P. McDermott. Effects of diet composition and ketosis on glycemia during verylow-energy-diet therapy in obese patients with non-insulin-dependent diabetes mellitus. Am J Clin Nutr 63: 110-115, 1996.
75. Halestrap, A. P. The mitochondrial pyruvate carrier. Kinetics and specificity for substrates and inhibitors. Biochem J 148: 85-96, 1975.
76. Hawkins, R. A., J. F. Biebuyck. Regional brain utilization of ketone bodies. In: Cerebral metabolism and neural function, edited by J. V. Passonneau, R. A. Hawkins, W. D. Lust, and F. A. Welsh. Baltimore: Williams & Wilkins, 1980, p. 255-263.
77. Hoshi, M., A. Takashima, M. Murayama, K. Yasutake, N. Yoshida, K. Ishiguro, T. Hoshino, K. Imahori. Non-toxic amyloid β peptide $_{1-42}$ suppresses acetylcholine synthesis. J Biol Chem 272: 2038-2041, 1997.
78. Hoshi, M., A. Takashima, K. Noguchi, M. Murayama, M. Sato, S. Kondo, Y. Saitoh, K. Ishiguro, T. Hoshino, K. Imahori. Regulation of mitochondrial pyruvate dehydrogenase activity by tau protein kinase I/glycogen synthase kinase 3beta in brain. Proc Natl Acad Sci U.S.A. 93: 2719-2723, 1996
79. Hutton, M., F. Busfield, M. Wragg, R. Crook, J. Perez-Tur, R. F. Clark, G. Prihar, C. Talbot, H. Phillips, K. Wright, M. Baker, C. Lendon, K. Duff, A. Martinez, H. Houlden, A. Nichols, E. Karran, G. Roberts, P. Roques, M. Rossor, J. C. Venter, M. D. Adams, R. T. Cline, C. A. Phillips, A. Goate. Complete analysis of the presenilin 1 gene in early onset Alzheimer's disease. Neuroreport. 7: 801-805, 1996.
80. Kashiwaya, Y., K. Sato, N. Tsuchiya, S. Thomas, D. A. Fell, R. L. Veech, J. V. Passonneau. Control of glucose utilization in working perfused rat heart. J Biol Chem 269: 25502-25514, 1994.
81. Kies, C., R. B. Tobin, H. M. Fox, M. A. Mehlman. Utilization of 1,3-butanediol and nonspecific nitrogen in human adults. J. Nutr. 103: 1155-1163, 1973
82. Kripke, S. A., A. D. Fox, J. M. Berman, J. DePaula, R. H. Birkhahn, J. L. Rombeau, R. G. Settle. Inhibition of TPN-associated intestinal mucosal atrophy with monoacetoacetin. J Surg Res 44: 436-444, 1988.
83. Langfort, J., W. Pilis, R. Zarzeczny, K. Nazar, H. Kaciuba-Uscilko. Effect of low-carbohydrate-ketogenic diet on metabolic and hormonal responses to graded exercise in men. J Physiol Pharmacol 47: 361-371, 1996.
84. Lawson, J. W. R., R. W. Guynn, N. W. Cornell, R. L. Veech. Gluconeogenesis, Its regulation in mammalian species. In: edited by R. W. Hanson and M. A. Mehlman, John Wiley & Sons: New York, 1976, p. 481-514.
85. Maiz, A., L. L. Moldawer, B. R. Bistrian, R. H. Birkhahn, C. L. Long, G. L. Blackburn. Monoacetoacetin and protein metabolism during parenteral nutrition in burned rates. Biochem J 226: 43-50, 1985.
86. Masuda, T., G. P. Dobson, R. L. Veech. The Gibbs-Donnan near-equilibrium system of heart. J. Biol. Chem 265: 20321-20334, 1990.
87. Mehlman, M. A., R. L. Veech. Redox and phosphorylation states and metabolite concentrations in frozen clamped livers of rats fed diets containing 1,3-butanediol and DL-carnitine. J Nutr 102: 45-51, 1972.
88. Nebeling, L. C., E. Lerner. Implementing a ketogenic diet based on medium-chain triglyceride oil in pediatric patents with cancer. J Am Diet Assoc 95: 693-697, 1995.
89. Nebeling, L. C., F. Miraldi, S. B. Shurin, E. Lerner. Effects of a ketogenic diet on tumor metabolism and nutritional status in pediatric oncology patents: two case reports. J Am Coll Nutr 14: 202-208, 1995.
90. Oster-Granite, M. L., D. L. McPhie, J. Greenan, R. L. Neve. Age-dependent neuronal and synaptic degeneration in mice transgenic for the C terminus of the amyloid precursor protein. J Neurosci 16: 6732-6741, 1996.
91. Owen, O. E., A. P. Morgan, H. G. Kemp, J. M. Sullivan, M. G. Herrera, G. F. Cahill, Jr. Brain metabolism during fasting. J Clin Invest 46: 1589-1595, 1967.
92. Paradis, E., H. Douillard, M. Koutroumanis, C. Goodyer, A. LeBlanc. Amyloid beta peptide of Alzheimer's disease downregulates Bcl-2 and upregulates bax expression in human neurons. J Neurosci 16:7533-7539, 1996.
93. Rhie, H. G., D. Dennis. Role of fadR and atoC(Con) mutations in poly(3-hydroxy-butyrate-co-3-hydroxyvalerate) synthesis in recombinant pha-*Escherichia coli*. Appl Environ Microbiol 61: 2487-2492, 1995.
94. Rossor, M. N. Catastrophe, chaos and Alzheimer's disease. The F E Williams Lecture. J R Coll Physicians Lond 29: 412-418, 1995.
95. Sato, K., Y. Kashiwaya, C. A. Keon, N. Tsuchiya, M. T. King, G. K. Radda, B. Chance, K. Clarke, R. L. Veech. Insulin, Ketone bodies, and mitochondrial energy transduction, FASEB J 9: 651-658, 1995.
96. Selkoe, D. J. Alzheimer's disease: genotypes, phenotypes, and treatments. Science 275: 630-631, 1997.
97. Sheng, J. G., K. Ito, R. D. Skinner, R. E. Mrak, C. R. Rovnaghi, L. J. Van Eldik, W. S. Griffin. In vivo and in vitro evidence supporting a role for the inflammatory cytokine interleukin-1 as a driving force in Alzheimer pathogenesis. Neurobiol Aging 17: 761-766, 1996.
98. Strittmatter, W. J., A. D. Roses. Apolipoprotein E and Alzheimer disease. Proc Natl Acad Sci U.S.A. 92: 4725-4727, 1995.
99. Taegtmeyer, H., R. Hems, H. A. Krebs. Utilization of energy-providing substrates in the isolated working rat heart. Biochem J 186: 701-711, 1980.
100. Talbot, C., H. Houlden, H. Craddock, R. Crook, M. Hutton, C. Lendon, G. Prihar, J. C. Morris, J. Hardy, A. Goate. Polymorphism in AACT gene may lower age of onset of Alzheimer's disease. Neuroreport. 7: 534-536, 1996.
101. Tobin, R. B., M. A. Mehiman, C. Kies, H. M. Fox, J. S. Soeldner. Nutritional and metabolic studies in humans with 1,3-butanediol. Fed Proc 34: 2171-2176, 1975.
102. Valentin, H. F., D. Dennis. Metabolic pathway for poly(3-hydroxybutyrate-co-3-hydroxyvalerate) formation in Nocardia corallina: inactivation of mutB by chromosomal integration of a kanamycin resistance gene. Appl Environ Microbio 62: 372-379, 1996.
103. Veech, R. L. The toxic impact of parenteral solutions on the metabolism of cells: a hypothesis for physiological parenteral therapy. Am J Clin Nutr 44: 519-551, 1986.
104. Veech, R. L. The untoward effects of the anions of dialysis fluids. Kidney Int 34: 587-597, 1988.
105. Veech, R. L., W. L. Gitomer. The medical and metabolic consequences of administration of sodium acetate. Adv Enzyme Regul 27: 313-343, 1988.
106. Veech, R. L., R. W. Guynn, D. Veloso. The time-course of the effects of ethanol on the redox and phosphorylation states of rat liver. Biochem J 127: 387-397, 1972.

107. Veech, R. L., R. L. Harris, M. A. Mehlman. Brain metabolite concentrations and redox states in rats fed diets containing 1,3-butanediol and ethanol.
Toxicol Appl Pharmacol 29: 196-203, 1974.
108. Wang, J. Z., I. Grundke-Iqbal, K. Iqbal. Restoration of biological activity of alzheimer abnormally phosphorylated tau by dephosphoryulation with protein phosphatase-2A, -2B and -1. Brain Res Mol Brain Res 38: 200-208, 1996.
109. Wilder, R. M. Effect of ketonuria on the course of epilepsy.
Mayo Clin Bull 2: 307-ff, 1921.
110. Williamson, D. H., P. Lund, H. A. Krebs. The redox state of free nicotinamide-adenine dinucleotide in the cytoplasm and mitochondria of rat liver.
Biochem J 103: 514-527, 1967.
111. Williamson, D. H., J. Mellanby, H. A. Krebs. Biochem J 82: 90-96, 1962.
112. Wing, R. R., H. A. Vazquez, C. M. Ryan. Cognitive effects of ketogenic weight-reducing diets. Int J Obes Relat Metab Disord 19: 811-816, 1995.
113. Zhang, H., V. Obias, K. Gonyer, D. Dennis. Production of polyhydroxylakanoates in sucrose-utilizing recombinant *Escherichia coli* and *Klebsiella* strains.
Appl Environ Microbiol 60: 1198-1205, 1994.

What is claimed is:

1. A method of producing a physiologically acceptable ketosis such as to treat a patient in need of therapy for one or more of Amylotrophic lateral sclerosis, and Duchenne's muscular dystrophy comprising oral administration to said patient of a ketogenic diet comprising a cyclic oligomer of formula (I)

where n is an integer of 1 or more
or a complex thereof with one or more cations or a salt thereof, wherein the physiologically acceptable ketosis is characterized by blood levels of (R)-3-hydroxybutyrate of from 0.5 to 20 mM.

2. A method as claimed in claim 1 wherein said patient is fed less than 50% by weight of its caloric content of its diet as fat.

3. A method as claimed in claim 1 wherein said patient is fed from 0 to 25% by weight or its caloric content of its diet as fat.

* * * * *